US006475996B1

(12) United States Patent
Cazaux et al.

(10) Patent No.: US 6,475,996 B1
(45) Date of Patent: Nov. 5, 2002

(54) USE OF A VECTOR EXPRESSING DNA POLYMERASE β AS MEDICINE

(75) Inventors: Christophe Cazaux, Plaisance du Touch; Gérard Jean Tiraby, Toulouse; Pascal Fons, Toulouse; Jean-Sébastien Hoffmann, Toulouse, all of (FR)

(73) Assignee: Centre National De La Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/319,265

(22) PCT Filed: Dec. 11, 1997

(86) PCT No.: PCT/FR97/02274

§ 371 (c)(1), (2), (4) Date: Jul. 6, 1999

(87) PCT Pub. No.: WO98/26077

PCT Pub. Date: Jun. 18, 1998

(30) Foreign Application Priority Data

Dec. 13, 1996 (FR) ............................................. 96 15343

(51) Int. Cl.[7] ........................ A01N 43/04; A01N 63/00; A61K 31/70; C12N 15/63; C12N 15/00
(52) U.S. Cl. ..................... 514/44; 424/93.2; 435/320.1; 435/455; 435/456; 435/325
(58) Field of Search ............... 424/93.1, 83.2; 435/69.1, 320.1, 6, 183, 325, 455, 456; 514/44

(56) References Cited

U.S. PATENT DOCUMENTS 5,614,365 A * 3/1997 Tabor et al. ..................... 435/6

FOREIGN PATENT DOCUMENTS

| EP | 0 293 491 | | 12/1988 |
|----|-----------|---|---------|
| WO | 91/07180 | | 5/1991 |
| WO | WO-96/21416 | * | 7/1996 |

OTHER PUBLICATIONS

Dang et. al., Gene Therapy and Translational Cancer Research, 1999; Clinical Cancer Research vol. 5: 471–474.*
Deonarain, Ligand–targeted receptor–mediated vectors for gene delivery, 1998; Exp. Opin. Ther. Patents, 8(1): 53–69.*
Rudinger, Characteristics of the amino acids as components of a peptide hormone sequence; 1976. In Peptide Hormones (Parsons, J.A., ed), University Park Press Baltimore, pp. 1–7.*
Ngo, Computational Complexity, Protein Structure Prediction, and the Levinthal Paradox, 1994. In The Protein Folding Problem and Tertiary Structure Prediction (Merz K. et al., eds), Birkhauser Boston, pp. 491–495.*

Miller et al., Targeted vectors for gene therapy, 1995; FASEB09: 190–199.*
Schwartz et al. A dominant positive and negative selectable gene for use in mammalian cells. Proc Natl Acad Sci. 88: 10460–10420, 1991.*
Ledley FD. Pharmaceutical Approach to Somatic gene therapy. Pharmaceutical Reseach. 13: 1595–1613, 1996.*
Verma et al. Gene Therapy—promises, problems and prospects. Nature. 389: 239–242, 1997.*
Bouayadi et al., "Overexpression of DNA polymerase beta sensitizes mammalian cells to 2'3'–deoxycytidine 3'–azido–3'–deoxythymidine" Cancer Res. 57: 110–116, 1997.
Caruso et al.,: Selective killing of CD4+ cells harboring a human immunodeficiency virus–inducible suicide gene prevents viral spread in an infected. Proc. Natl. Acad. Sci., vol. 89, No. 1, (1992), pp. 182–186.
Parker et al.,: Mechanism of inhibition of human immunodeficiency virus type I reverse transcriptase and human DNA 5'–triphosphatase of carbovir, 3'–azido3'deoxythmidine 2'3'dideoxyguanosine, and 3'–deoxythmydine J. Biol. Chem., vol. 266, No. 3, (Jan. 1991), Am.Soc. Biochem. Mol., INC. Baltimore. US, pp. 1754–1762.
Copeland et al.,: Human DNA polymerase alpha and beta are able to incorporate anti–HIV deoxynucleotides into DNA, J. Biol chem., vol. 267, No. 30, (Oct. 1992) Am. Soc. Biochem Mol. Biol., Inc. Baltimore, U.S., pp. 21459–21464.
Fornace et al.,: Induction of beta–polymerase mRNA by DNA–damaging agents in chinese hamster ovary cells Mol. Cell. Biol., vol. 9, No. 2, Feb. 1989, ASM Washington, DC, US, pp. 851–853.
Srivastava et al.,: "Phorbol ester abrogates up–regulation of DNA polymerase beta by DNA–alkylating agents in chinese hamster ovary cells" J. Biol. Chem., vol. 270, No. 27, Jul. 7, 1995, Am. Soc. Biochem. Mol.Biol.Inc., Baltimore,US, pp. 16402–16408.
Sobol et al.: "Requirement of mammalian DNA polymerase–beta in base–excision repair" Nature, vol. 379, (Jan. 1996), Macmillan Journals Ltd. London, UK, pp. 183–186.
M. Caruso: "Gene Therapy Agains Cancer and HIV Infection Using the Gene Encoding Herpes Simple Virus Thymidine Kinase" Molecular Medicine Today, vol. 2, No. 5 (May 1996), pp. 212–217.

* cited by examiner

Primary Examiner—Dave T. Nguyen
Assistant Examiner—Quang Nguyen
(74) Attorney, Agent, or Firm—Foley & Lardner

(57) ABSTRACT

The invention concerns the use of a vector expressing DNA polymerase β for the treatment of cancer or viral diseases such as AIDS.

13 Claims, 6 Drawing Sheets

FIG_1

FIG_2

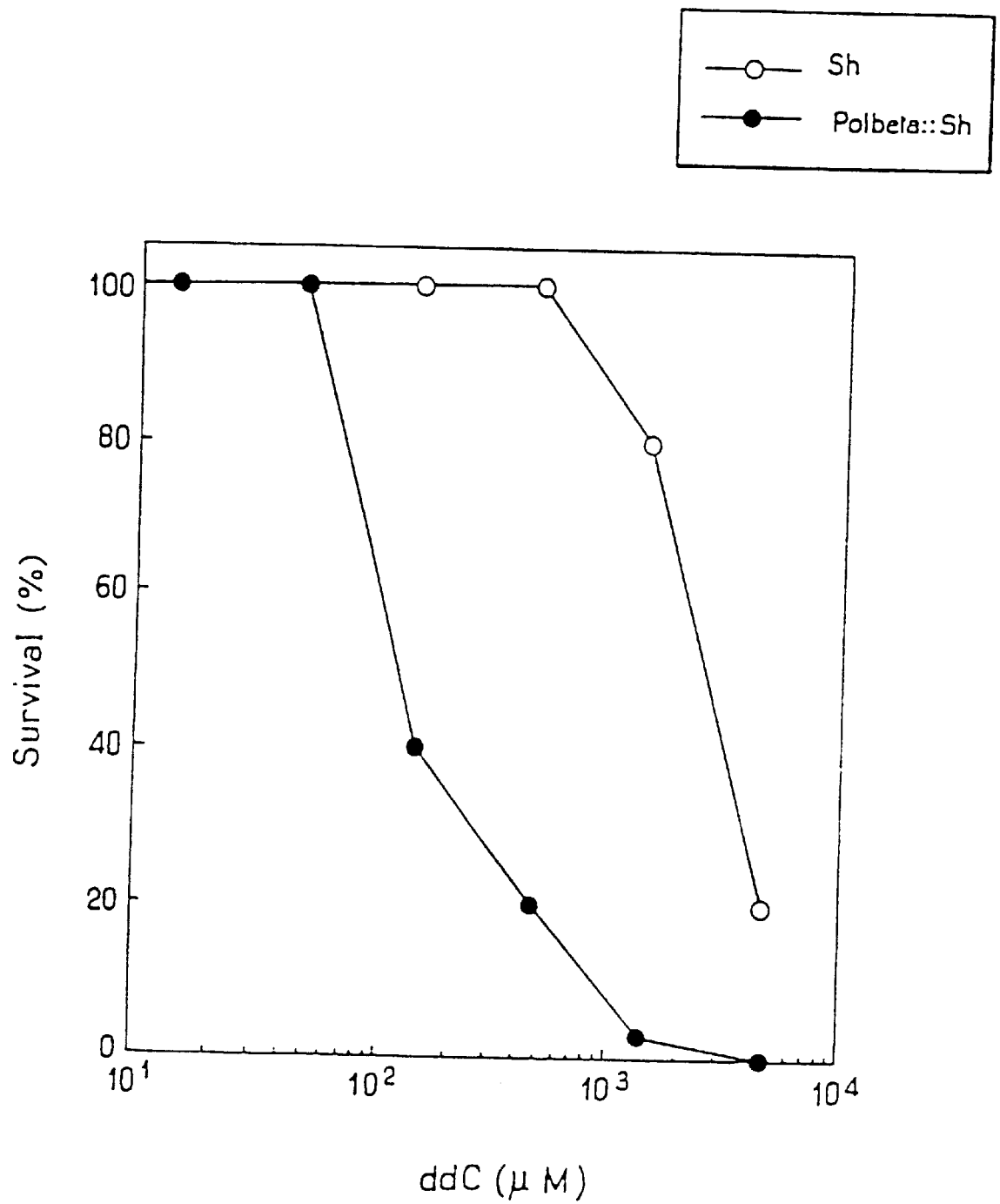
FIG_4

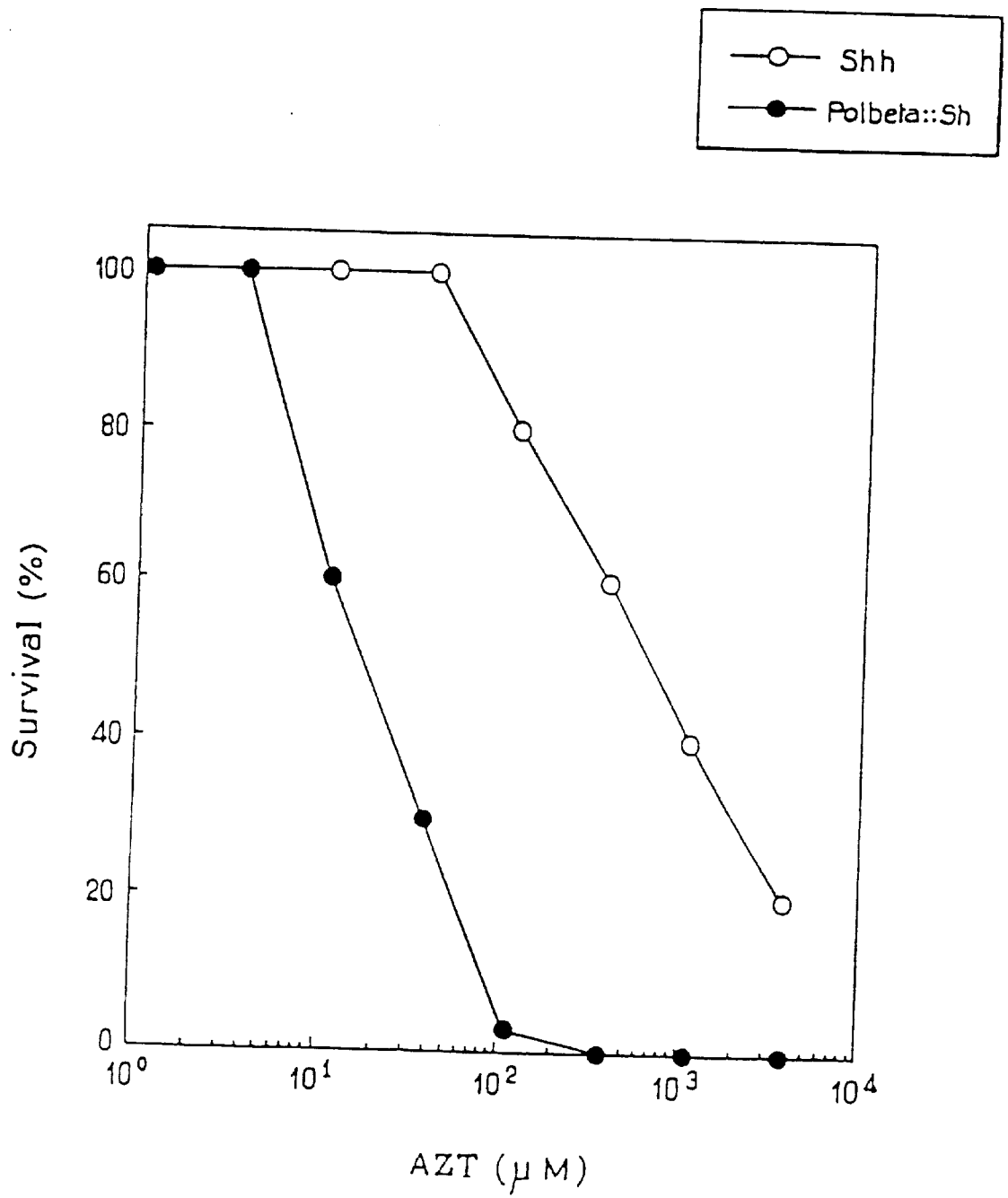
FIG_5

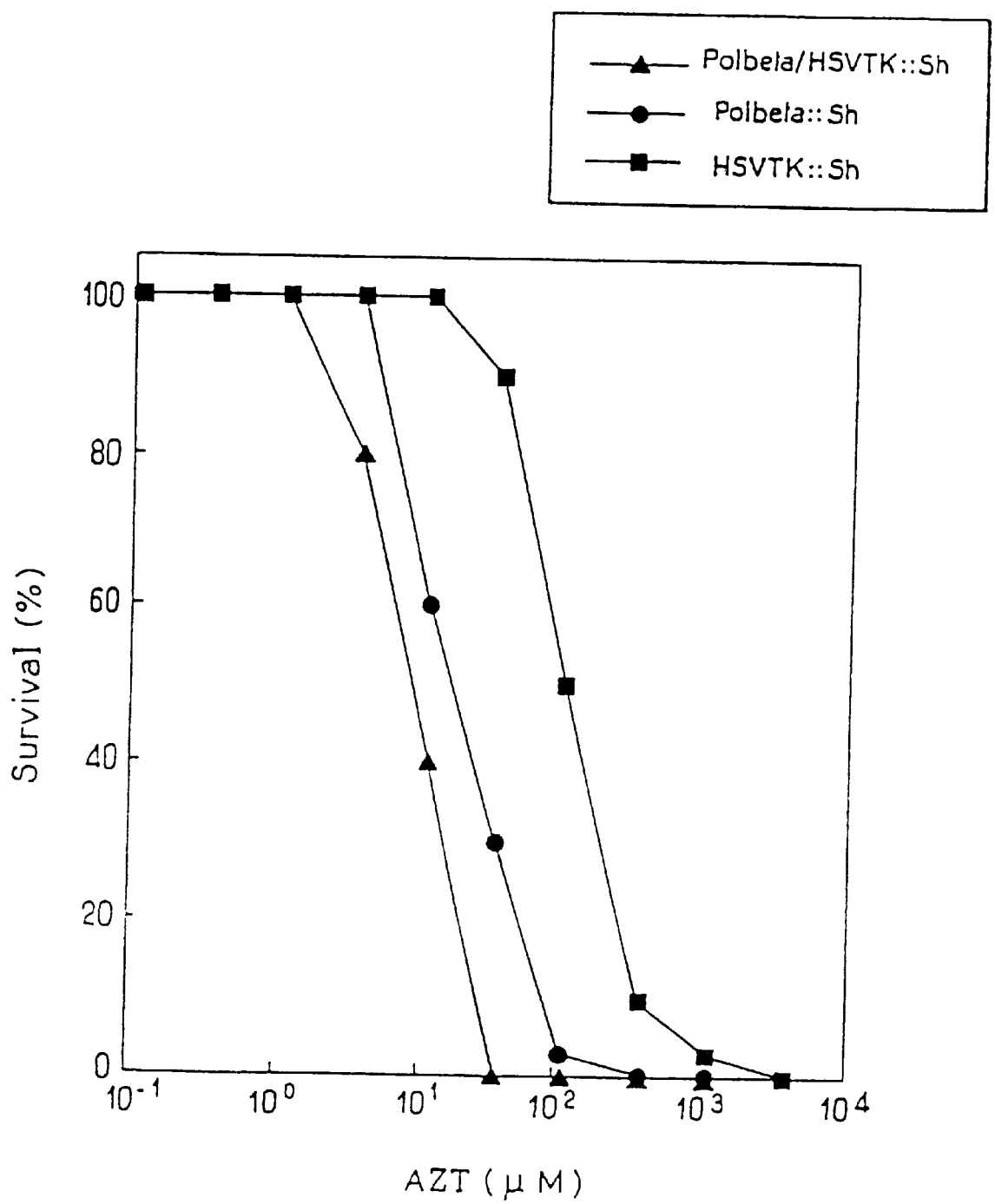
FIG_6

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 1
tattccatgg cactcgtgga actcgcaaac ttt                                       33

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 2
ttaagctagc tcactcctgt ccttgggctc                                           30

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide for PCR

<400> SEQUENCE: 3
ttctcagtga ccggcgccta gt                                                   22

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide for PCR

<400> SEQUENCE: 4
gggagcccaa ggacaggagt gaatgattcg aacttt                                    36

<210> SEQ ID NO 5
<211> LENGTH: 17
<212> TYPE: DNA
<213> ORGANISM: Artificial Sequence
<220> FEATURE:
```

```
<223> OTHER INFORMATION: Description of Artificial Sequence: G-rich
      nucleotide substrate

<400> SEQUENCE: 5
tacaaccaag agcatac                                                              17

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: G-rich
      nucleotide substrate

<400> SEQUENCE: 6
ggtggtggtg ggcgccggcg gtgtgaattc ggcactggcc gtcgtatgct cttggttgta         60
```

USE OF A VECTOR EXPRESSING DNA POLYMERASE β AS MEDICINE

BACKGROUND OF THE INVENTION

The present invention relates to the use of a vector which expresses DNA polymerase β as a DNA medicinal product in the context of the molecular treatment of cancer and viral diseases such as AIDS.

Essentially two types of genetic treatment exist for these diseases, namely immunotherapy and the introduction of "suicide" genes by viral vectors into the target cells.

Genetic immunotherapy is the use of tumor-infiltrating lymphocytes (TILs), which are highly tumoricidal. When they are transformed, they convey interleukin (IL2, IL4, IL6, γ-interferon) genes to the tumor and these activate the immune response locally, allowing both a limitation of the side effects on the body and an amplification of their antitumor effect.

The approach directed toward transferring a "medicinal DNA" or therapeutic gene into a tumor cell has already been proposed (Culver et al., 1994) in the context of the use of genes such as the HSV tk gene of thymidine kinase from the human herpesvirus HSV-1 (Moolten et al., 1990; Culver et al., 1992) or VZV tk if it is from the chickenpox virus (Huber et al., 1991), the bacterial genes gpt coding for xanthine/guanine phosphoribosyl-transferase (Mroz et al., 1993) or codA coding for cytosine deaminase (Mullen et al., 1992). The products of these "suicide" genes convert initially nontoxic agents, such as ganciclovir (GCV) in the case of HSV-TK, 6-methoxypurine (ara-M) with VZV-TK, 5-fluorocytosine (5-FC) with CodA and 6-thioxanthine (6-TX) with GPT, into products which are highly toxic to the cell.

Viral thymidine kinase (TK) genes have been used in particular to destroy several types of cancer cells (Moolten et al., 1990; Huber et al., 1991; Vile et al., 1993), making these cells sensitive to purine or pyrimidine analogs such as acyclovir (ACV), ganciclovir (GCV) or bromovinyldeoxyuridine (BVDU). These nucleoside analogs are converted by the viral TKs into diphosphorylated forms which are then triphosphorylated with endogenous cell enzymes before incorporation into the tumoral DNA by DNA polymerases. The incorporation of these chain terminators (absence of 3' OH) blocks the replication of the DNA and leads to cell death.

DETAILED DESCRIPTION OF INVENTION

The present invention proposes to use a novel type of suicide gene whose function consists in facilitating the incorporation of a nucleotide analog into the DNA of the target cell after phosphorylation of the nucleoside prodrug optionally by a "standard" suicide gene.

The incorporation of nucleotides into DNA is naturally carried out in eukaryotic cells by DNA polymerases. Among the mammalian DNA polymerases, DNA polymerase β has a number of specific features.

DNA polymerase β is a polypeptide of 39 kD and is an enzyme which is highly conserved in higher eukaryotes (Kornberg et al., 1992). Its primary function is believed to be the repair of damaged DNA (Sobol et al., 1996), but it also has a role in the replication of native DNA (Jenkins et al., 1992; Sweasy et al., 1992). DNA polymerase β is expressed at a constant level during the cell cycle (Zmudzka et al., 1988) and exposure of the cell to xenobiotic agents such as radiations induces its expression (Srivastava et al., 1995; Fornace et al., 1989). It differs from the other polymerases in its small size and its unfaithful nature during DNA replication, this infidelity being linked to the absence of associated corrective exonuclease activities (Kunkel et al., 1986).

in vitro, it has been shown that DNA polymerase β incorporates ddCMP (triphosphorylated dideoxycytidine), an inhibitor of DNA synthesis, with an efficacy which is comparable to that observed for the incorporation of the natural antagonist dCMP or deoxycytidine monophosphate (Copeland et al., 1992). Very similar results have been published in relation to AZT (Copeland et al., 1992; Parker et al., 1991). in vivo, AZT-MP (azidothymidine monophosphate) is in fact incorporated into cellular DNA (Sommadossi et al., 1989) and it has been suggested that DNA polymerase β plays a role in this process (Parker et al., 1991).

Thus, a subject of the present invention is, in particular, the use of a vector which expresses DNA polymerase β or an analog of DNA polymerase β in order to incorporate nucleotide analogs with antiviral or antitumor activity into a cell's DNA, for the manufacture of a medicinal product intended for the treatment of cancer or a viral disease such as AIDS.

The expression "DNA polymerase β analog" means any nucleotide sequence which has at least 80% homology with the nucleotide sequence of mammalian DNA polymerase β and which fulfils the same functions.

The present invention thus consists in inducing an intracellular overproduction of an enzyme which is normally present in low amount in the cell, namely DNA polymerase β, in order to amplify its unfaithful and mutagenic nature and thus force the incorporation of nucleotide analogs into the DNA.

A subject of the present invention is also an expression vector comprising a gene coding for DNA polymerase β or an analog of DNA polymerase β. The vector is intended to express DNA polymerase β in tumor cells or cells infected with a virus such as the AIDS virus. It is thus advantageous to place said gene under the control of an expression system which is effective in the target cells.

According to one advantageous embodiment of the present invention, the expression vector in accordance with the present invention comprises a target sequence and/or expression sequence which is specific for tissues in which it is desired to express the DNA polymerase β (or an analog), such as tumors or tissues infected with viruses; by way of example, mention may be made of hematopoietic strain cells for the eradication of CD4$^+$ lymphocytes infected with the HIV virus.

The expression vector according to the present invention can be any vector commonly used in gene therapy, and particularly a viral vector derived from a virus chosen from adenoviruses, adeno-associated viruses, retroviruses (including HIV), herpesviruses, poxviruses, parvoviruses, plasmoviruses, Semliki Forest viruses and Sindbis viruses.

As indicated above, DNA polymerase β allows the incorporation of nucleotide analogs into DNA. Now, certain nucleoside analogs are known to have antiviral activity when they are phosphorylated, i.e. in the form of nucleotides. This is the case in particular for AZT and ddC. These nucleoside analogs are normally atoxic to cells. However, after phosphorylation and in the presence of DNA polymerase β (or analog), they are incorporated into DNA and block its replication. The phosphorylation in question can be carried out in particular by thymidine kinase and/or thymidilate kinase.

Thus, according to one particularly advantageous embodiment, the use of a vector which expresses DNA polymerase β (or analog) in accordance with the present invention can be potentiated by the expression, in these same target cells or tissues, of the thymidine kinase and/or thymidilate kinase gene.

The cells in which the DNA polymerase β and the thymidine kinase and/or thymidilate kinase are expressed are thus made more sensitive to nucleoside analogs such as AZT or ddC, which, in situ, are phosphorylated before being incorporated into the DNA.

The thymidine kinase and/or thymidilate kinase gene can be inserted on the same vector as the one which expresses DNA polymerase β or on another vector. In the latter case, the target cell will undergo a co-transfection in order to allow the expression of each of the genes concerned. In any case, the gene coding for thymidine kinase and/or thymidilate kinase will be placed under the control of an expression system which is effective in the target cells to be reached.

The subject of the present, invention is also cells transformed with an expression vector in accordance with the invention comprising a gene coding for DNA polymerase β (or analog) and optionally also comprising a gene coding for thymidine kinase and/or thymidilate kinase, as well as to the cells transformed with an expression vector in accordance with the invention comprising the two abovementioned genes.

Moreover, it should be pointed out that the vectors in accordance with the present invention can be used as cloning vectors. The insertion of a polylinker into the gene coding for DNA polymerase β (or an analog) without modifying the reading frame, which is itself inserted into a vector such as pUT-pol β or pZHTk β, allows a gene of interest to be cloned. The recombinant cells transfected with this type of vector can readily be selected since they have become resistant to nucleoside analogs such as AZT or ddC following inactivation of the DNA polymerase β (or analog) gene.

Lastly, a subject of the present invention is a product containing an expression vector according to the invention comprising a gene coding for DNA polymerase β (or analog) and a gene coding for thymidine kinase and/or thymidilate kinase or two expression vectors each comprising one of the genes in question and at least one antiviral agent, as a combination product for simultaneous or separate use or for use spread out over time. Preferably, the antiviral agent is AZT or ddC.

It should also be noted that the use of expression vectors and/or cells transformed with these expression vectors, in accordance with the present invention in the context of the treatment of cancers or viral diseases such as AIDS, can be combined with any other standard treatment such as chemotherapy or radiotherapy.

BRIEF DESCRIPTION OF THE DRAWINGS

FIG. 4 illustrates the comparison, as a percentage of survival, of B16 cells transfected with the vector pUT-pol β or with a control vector pUT 526 Δ in the presence of ddC.

FIG. 5 illustrates the comparison, as a percentage of survival, of B16 cells transfected with the vector pUT-pol β or not with the vector pUT-pol β in the presence of AZT.

FIG. 6 illustrates the comparison, as a percentage of survival, of B16 cells transfected with a vector which expresses DNA polymerase β, with a vector which expresses thymidine kinase and thymidilate kinase activities or with a vector which expresses both.

Figure 1:
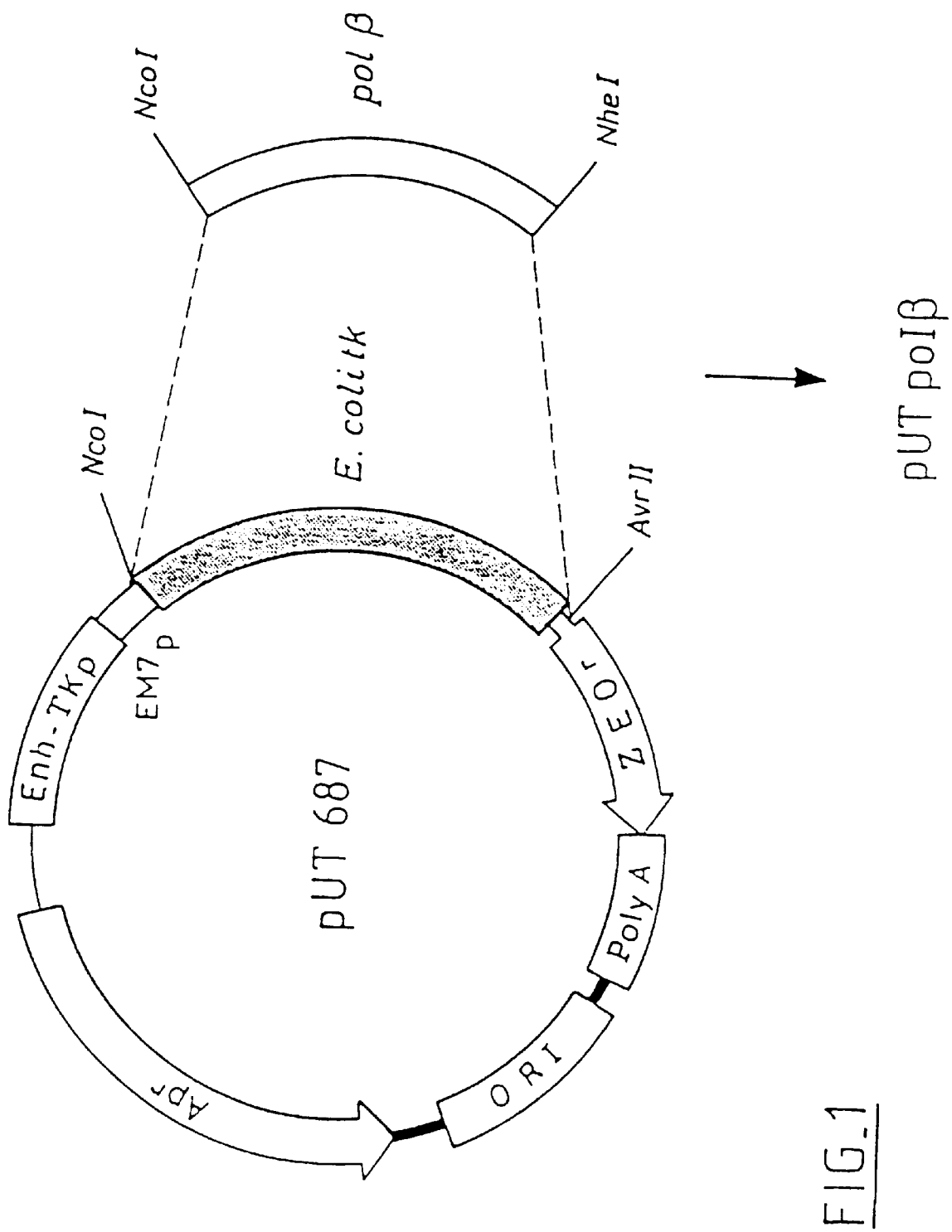
FIG. 1 represents the construction of the vector pUT-pol β from the vector pUT 687.

The present invention is not limited to the abovementioned description, but, rather, encompasses all the variants; furthermore, it will be understood more clearly in the light of the examples below, which are given purely for illustrative purposes.

EXAMPLES

EXAMPLE 1

Construction of a plasmid vector which overexpresses DNA polymerase β.

Materials:

AZT (Retrovir IV, zidovudine, Azidothymidine) and Ganciclovir (Cymevan) are obtained from the laboratories of Wellcome, Paris and Syntex, Puteaux, S.A., respectively.

Zeocine is produced by the company CAYLA, Toulouse.

The information regarding the *E. coli* bacterial trains used is collated in the table below:

| Strains | Genotypes | Sources |
|---------|-----------|---------|
| MC 1061 | D(ara leu) aral galU galK hsdS rpsl.Δ(lac IOPZYA)X74 ΔrecA | O. Fayet (IBCG, University of Toulouse III) |
| SC 18-12 | Ion11, sulA 1, trpE65, uvrA 155, fadAB::Tn10, recA178, polA12 | Witkin (Waksman Institute, State University, New Jersey) |

Culture media:

Complete LB medium (per liter): tryptone 10 g, yeast extract 5 g, NaCl 10 g, agar 15 g, $H_2O$ qs 1 l.

M9CA minimum medium (per liter): $Na_2HPO_4.2H_2O$ 8.5 g, $KH_2PO_4$ 3 g, NaCl 0.5 g, $NH_4Cl$ 1 g, 0.4% glucose, 0.2% caseine hydrolyzate, agar 1.5 g, $H_2O$ qs 1 l.

NA medium (per liter): "Bacto Nutrient Agar" from Difco, Bacto Beef Extract 3 g, Bacto Peptone 5 g, NaCl 10 g, agar 15 g, $H_2O$ qs 1 l.

Transformation:

Competent cells are prepared according to the Kushner method. 25 ml of sterile LB are inoculated with the strain and, at $OD_{600}$=0.4, centrifuged for 15 minutes at 5000 rpm, at 4° C. The cells are taken up in 2.5 ml of 0.1 M $CaCl_2$/10 mM MOPS/0.5% cold glucose left for 30 minutes at 0° C. 100 μl of competent cells are incubated with the plasmid DNA (volume less than 10 μl, 10 to 50 ng per ccc plasmid) for 30 minutes in ice and then for 5 minutes at 42° C. without stirring. LB medium is then added at room temperature (qs 1 ml) and the cells are placed at 37° C. (MC 1061) or at 30° C. (heat-sensitive SC 18-12) with stirring (New Brunswick, 300 rpm) for 1 h 30 min for the phenotypic expression, and are then plated out on Amp selective medium (LB+ Ampicillin 100 μg/ml) for the vector pUT, or on Zeo elective medium (LB+Zeocine 20 μg/ml) for the vector TG.

Cloning:

The DNA fragments obtained from the appropriate enzymatic digestions are separated by electrophoresis on Sea Plaque low-melting agarose gel (FMC) at 0.7% in TAE buffer (0.004 M Tris-acetate/0.001 M EDTA). The bands chosen are cut up, liquefied in TE 1× adjusted to 0.5 M NaCl and the mixture is heated for 10 minutes at 70° C. The DNA solutions are then purified by extraction with phenol-CHISAM and then precipitated with one volume of isopropanol+1 µl of glycogen. The pellets are then dried and taken up in the minimum volume of sterile water (10 µl). The required DNA fragments are mixed and incubated in a ligation buffer (66 mM Tris-HCl, 5 mM MgCl$_2$, 1 mM polyethylene glycol, 1 mM ATP, pH 7.5) with one unit of T4 phage ligase (20 µl final) at 16° C. overnight. The ligation product is then used to transform the adequate strain. The adapted selection is either resistance to 100 g/ml ampicillin or to 20 µg/ml Zeocine, depending on the plasmid.

Extraction of the plasmid DNA:

The plasmids are prepared according to the method of Birboim and Doly (Birboim et al., 1979) by alkaline lysis of the bacteria from streaks on dishes or from 25 ml cultures. The plasmid DNA of the transformants is extracted and checked by restriction analysis.

Standard PCR conditions:

The polymerase chain reaction is carried out in 500 µl microtubes containing 5 µl of 150 µM MgCl$_2$ buffer, a mixture of the 4 dNTPs (250 µM each), 10 ng of matrix DNA and 500 ng of each oligonucleotide primer in a reaction volume of 100 µl, to which 2 to 3 drops of oil are added to prevent any evaporation. After 7 minutes of pre-denaturation at 95° C., 2.5 units of Tfl Polymerase enzyme (EPICENTRE) are added "Hot-Start". The amplification is obtained after 25 cycles of denaturation (94° C., 1 min), hybridization (55° C., 1 min) and extension with polymerase (72° C., 1.5 min).

The primers used consist of two parts: a part which hybridizes with one end of the gene to be cloned and a non-hybridizing part which includes a restriction site which is compatible with the cloning site in the expression vector. Purification of the PCR product by electrophoresis on Sea Plaque low-melting 0.7% agarose gel (TEBU) and controlled by enzymatic digestion. The ends are cleaved and ligated inside the complementary sites of the expression plasmid (Enzymes Biolabs and Boehringer).

Rat polymerase beta gene:

The cDNA of purified rat DNA polymerase was generously donated by Dr Wilson (Galveston, Tex., USA). The sequence of this gene was obtained by the EMBL European Data Bank.

Vector:

A vector was constructed in which the CDNA of the rat polymerase gene was cloned after amplification by the PCR technique. pUT-Pol β

The plasmid pUT-Pol β results from replacement of the *E. coli* thymidine kinase gene (fragment NcoI-AvrII) with polymerase β (fragment NcoI-NheI) fused with the Zeocine-resistance gene in the plasmid pUT 687. The polymerase β gene is placed under the control of two strong constitutive promoters in tandem, the bacterial promoter EM7 and the eukaryotic promoter of the TK gene from HSV with its enhancer, known as the "shuttle" vector, which can be used in *E. coli* and in eukaryotic cells (FIG. 1).

5' primer: Addition of 2 CA bases allowing the rat polymerase β gene to be introduced in the open reading frame. These 2 bases create a codon GCA coding for an Alanine. The site Nco I provides the construct with the site for initiation of the ATG translation.

3' primer: loss of the single restriction site Avr II from the plasmid during Avr II/Nhe I ligation.

Loss also of the "Stop" codon for the polymerase β gene to allow fusion of this gene with the Zeocine-resistance gene, a counterselection of the AZT clones will allow the clones which have lost the *E. coli* thymidine kinase to be selected. Summary of the construction of the vector pUT-pol β:

| Vector constructed | PUT - Pol β |
|---|---|
| Parental vector | pUT 687 |
| | *E. coli* thymidine |
| | kinase::zeo |
| Resistance provided | Zeocine |
| | (if the fusion is correct) |
| | Ampicillin |
| Gene cloned | rat polymerase β cDNA |
| 5' PCR primer | 5' TAT <u>TCC</u> <u>ATG</u> GCA CTC GTG |
| | GAA CTC GCA AACTTT 3' (SEQ ID NO: 1) |
| Restriction site supplied | Nco I:  CC ATG G |
| | GG TAC C |
| 3' PCR primer | 5' TTA A<u>GC TAG</u> CTC ACT CCT |
| | GTC CTT GGG CTC 3' (SEQ ID NO: 2) |
| Restriction site supplied | Nhe I:  <u>GCT AGC</u> |
| | CGA TCG |
| Ligation | 5' Nco I/Nco I |
| | 3' nhe I/Avr II |

Determination of the MIC (minimum inhibitory concentration):

The cells are plated out on solid LB medium overnight. They are taken up in 1 ml of LB medium containing 20% glycerol final and stored at −700° C. 5 µl of a suspension of 0.5 ml of M9CA medium are inoculated with an estimated constant amount of frozen cells taken up with a platinum loop so as to obtain an OD$_{600}$=0.1–0.2, and deposited on M9CA medium containing increasing concentrations of drug. After leaving overnight at 37° C., the lethal concentration is noted for the different strains.

Survival tests:

The survival test makes it possible to demonstrate sensitization of the strain to the drug by DNA polymerase β.

*E. coli* B/R SC 18-12 bacteria are incubated overnight in 25 ml of liquid NA medium with 35 µg/ml ampicillin, at 30° C. with stirring (New Brunswick 300 rpm), diluted so as to obtain an OD$_{600}$=0.1–0.2 in 20 ml of NA medium, and recultured under the same conditions as above until an OD$_{600}$=0.4 is obtained, they are then diluted 10$^5$-fold in liquid M9CA medium, 100 µl are plated out on M9CA dishes containing different concentrations of drug, and incubated for 1 to 2 days at 37° C. or at 30° C. The number of colonies is counted on each of the dishes, and the percentage of survival is determined relative to the maximum value of the drug-free control dish.

In parallel, RecA polA12 mutant *E. coli* SC 18-12 strain was transformed with the vector pUT-Pol β. DNA polymerase I is heat-sensitive at 37° C., but functions at 30° C. The overexpression of DNA polymerase β, at a non-permissive temperature of 37° C., restores the viability, as expected.

The plasmids of these bacteria were extracted, digested with Eco RI and the electrophoretic profiles were checked. We also carried out a control by PCR with the probes used for the cloning, and the DNA polymerase β gene is indeed borne by plasmids extracted from the test bacteria.

Another bacterial strain MC 1061 was also transformed by the vector pUT-Pol β, in order to observe a change in the minimum inhibitory concentration with AZT and Ganciclovir, mediated by DNA polymerase β.

1—Strain MC 1061/pUT-pol β

With respect to AZT:

The "spots" obtained on the dishes for the bacteria MC 1061-pUT-Pol β show that, with respect to AZT, the value of the MIC goes from 0.03 µg/ml for the parent control strain to 0.001 µg/ml (factor 30), without the presence of the thymidine kinase-HSV1 suicide gene. The AZT is toxic to the bacteria.

The results are collated in Table 1 below.

TABLE 1

Minimum inhibitory concentrations (µg/ml):

| | AZT Azidothymidine |
|---|---|
| MC 1061 - TK+ non-transformed | 0.03 |
| MC 1061 - TK+ pUT - Pol β | 0.001 |

2—Strains SC 18-12/pUT-pol β

Figure 2:
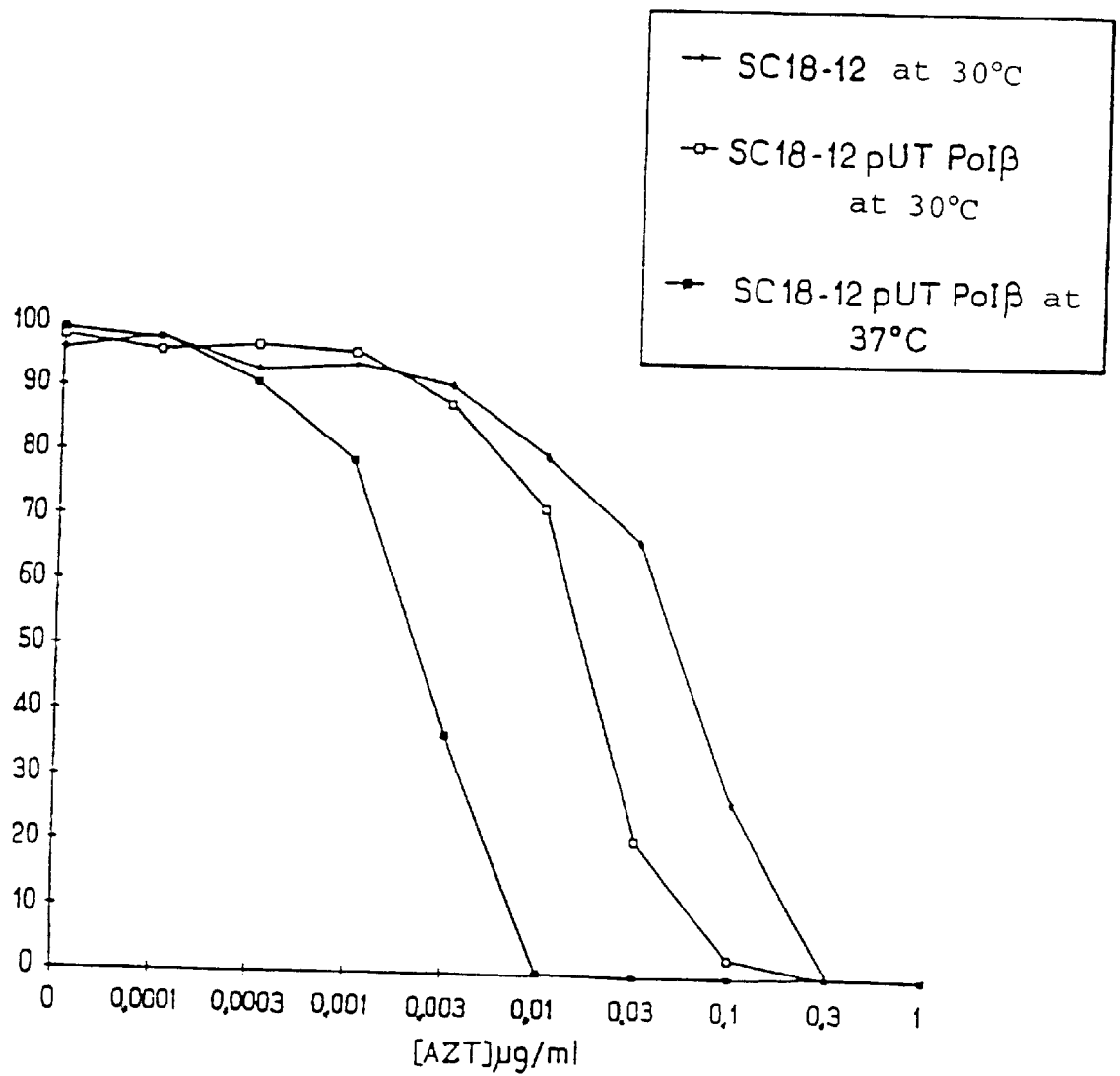
FIG. 2 represents the percentage of survival of *E.coli* SC 18-12 cells transformed with the vector pUT-pol β at different temperatures, in the presence of AZT.

With respect to AZT (FIG. 2):

The experiment at 37° C. shows a dose/response effect for AZT, as expected. The MIC falls with the strain SC 18-12/pUT-Pol β by a factor of 3 at 30° C. and by a factor of 30 at 37° C., relative to the parent strain at 30° C. This confirms the functionality of our vector and shows that the "suicide" effect of DNA polymerase β in bacterial cells exists.

EXAMPLE 2

CHO or B16 animal cells which overexpress Pol β become sensitive to ddC and to AZT.

Culture media:

The materials are obtained from Biowhittaker. Heraeux oven at 37° C., 5% $CO_2$.

CHO: the Chinese hamster ovary cells (Line supplied by J. Tessié-IBCG-Toulouse) are cultured in L-glutamine-free α-MEM-HEPES medium supplemented with calf fetal serum (10% FCS), L-glutamine, penicillin/streptomycin (PS 50 µg/ml).

B16: the mouse melanoma cells (Line B16b16 supplied by S. Cros-I.P.B.S.-Toulouse) are cultured in an RPMI 1640 medium, supplemented with horse serum (10% HS), penicillin/streptomycin (PS 50 µg/ml).

Transfection of the CHO/B16 cells:

The technique used for the 2 types of cell is identical; only a few parameters are different.

A number of confluent cells (CHO=$2\times10^5$/B16=$4\times10^5$) are placed in 2 ml of supplemented medium. At 24 hours the cells at subconfluence are washed with PBS and placed in 1 ml of serum-free medium containing 10 µl of Aldrich polybrene (1-/-) and 10 µg of DNA. At 30 hours for the CHO and at 40 hours for the B16, the cells are subjected to a DMSO shock (1 ml 30% DMSO for 3–4 minutes), 2 rinses with serum-free medium, incubation for 72 hours and addition of the Zeocine selection (CHO 100 µg/ml; B16: 10 µg/ml).

Recovery of the clones:

About 15 days for the CHO (3 to 4 weeks for the B16) after washing with PBS, the clones are recovered by scraping with a micropipette in 5 µl of medium, and are deposited individually or as a "pool" in a dish with a diameter of 35 mm containing 2 ml of medium supplemented with Zeocine (100 or 10 µg/ml).

Determination of the MIC (minimum inhibitory concentration)

The confluent cells are detached with trypsin after rinsing with PBS (phosphate buffer saline/Biowittaker) and are taken up in 1 ml of suitable medium with serum and antibiotics.

1 ml of supplemented medium is added to each well (24-well Nunc plate) along with 2000 cells for the CHO or B16, and the various prodrugs of increasing concentrations.

A first reading of the MIC values is taken after 5 days for the CHO and 7 days for the B16; the medium is replaced with a drug-free medium and the true MIC is determined at 10 and 14 days, respectively.

Studies of the toxicity of DNA polymerase β overexpressed in eukaryotic CHO and B16 cells:

DNA polymerase β is a constitutive eukaryotic enzyme, known as a "house-keeping" enzyme. A constitutive overexpression of this polymerase should not present too large a toxicity for the transfected cells. The two types of cell (CHO and B16) were transformed with the vectors. In the two cases, the plasmid introduced cannot be replicated and must be integrated randomly into the cell genome. For these reasons, a pool of 5 clones of CHO was also tested in order to have a precise and overall confirmation on this type of cell.

The vector pUT-Polβ shows that the overexpression of DNA polymerase β alone is certainly not toxic to the cell during division, since we have obtained many clones. The most surprising result is that this eukaryotic polymerase by itself very markedly sensitizes the eukaryotic CHO cells to AZT (MIC from 10 to 30 µg/ml), with a factor of greater than 30 for 3 out of 5 clones.

The results are summarized in Table 2 below.

TABLE 2

Minimum inhibitory concentrations for the CHO cells (µg/ml)

| | AZT Azidothymidine |
|---|---|
| Non-transfected/zeo | >300 |
| pUT: Polymerase β.//zeo | 10/30 |

EXAMPLE 3

Construction of an expression vector bearing both polβ and the HSV tk thymidine kinase gene from the human herpesvirus HSV-1 which codes both for thymidine kinase activity and thymidilate kinase activity.

Figure 3:
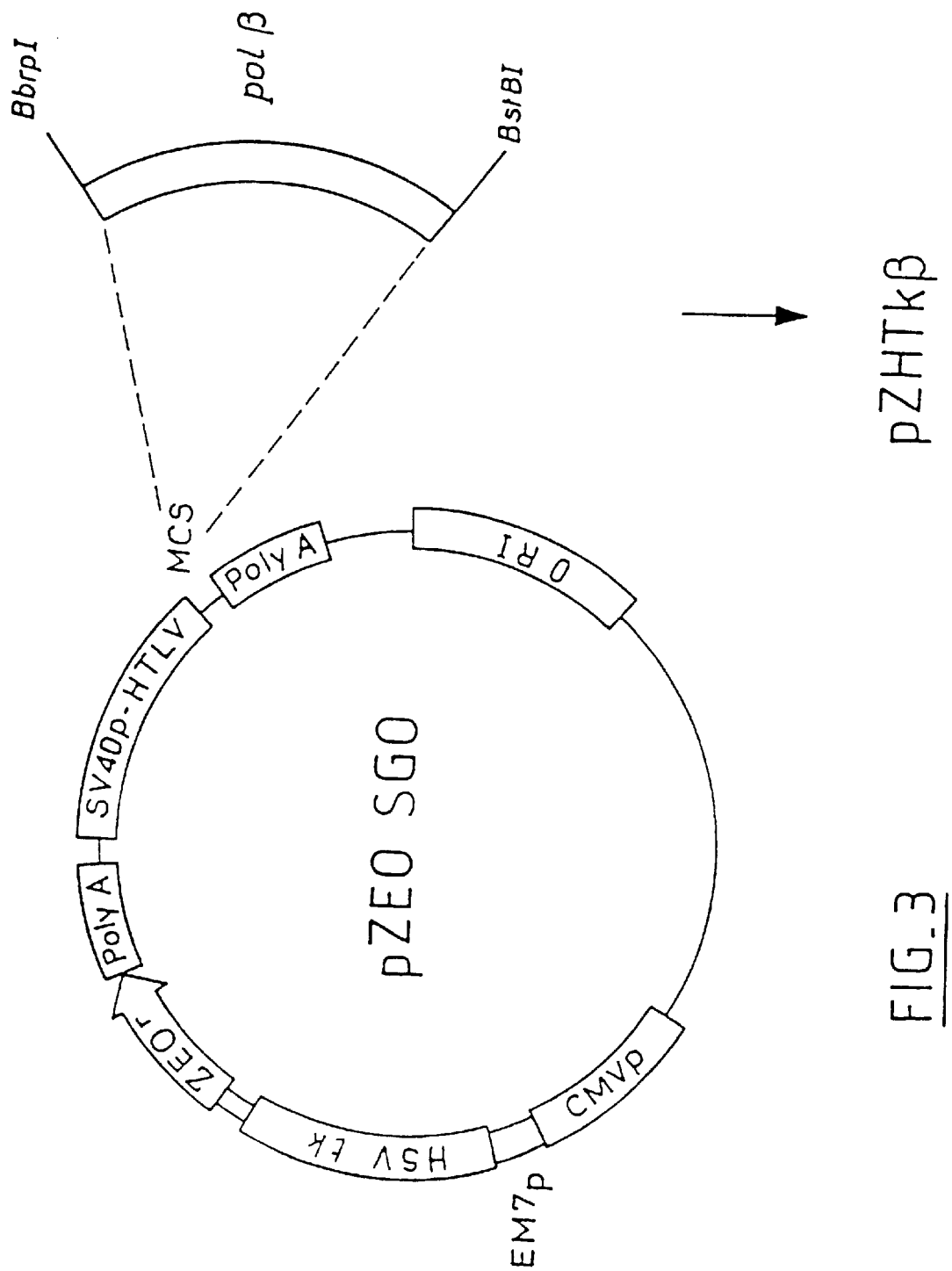
FIG. 3 represents the construction of the vector pZHTk β from the vector pZEOSGO.

The plasmid pZHTkβ (FIG. 3) was constructed by amplifying a fragment of pUT-pol β containing pol β, by PCR by means of the use of the oligonucleotides:

5' TTCTCAGTGACCGGCGCCTAGT 3' (SEQ ID NO:3)

5' GGGAGCCCAAGGACAGGAGTGAATGAT-TCGAACTTT3' (SEQ ID NO:4)

After BbrpI-BstBI cleavage, the PCR fragment was inserted into a vector pZEOSGO opened with SpeI-BstBI and then treated with Klenow polymerase at the SpeI end. pZEOSG0 is derived from pZEOSV1 (Cayla, VECT 2001).

The functionality of the construct was checked using *E. coli* bacterial strains, 1—either by transforming the strain SC 18-12 for the expression of pol β, 2—or by transforming a strain SC 18-12 tk⁻ which is deficient for thymidine kinase activity, for the HSV TK thymidine kinase expression. The mutant tk⁻ was obtained by plating out SC 18-12 bacteria on a medium containing AZT. Only the cells deficient in TK activity grow on such a medium, since the AZT is not phosphorylated in this case and thus cannot be incorporated into the DNA, 3—or by transforming the strain TD205, a heat-sensitive mutant for thymidilate kinase activity, for the HSV TK thymidilate kinase activity.

Table 3 below shows that the sensitivities of the strains used to zeocine, to AZT or to a non-permissive temperature are suppressed after transformation with the plasmid bearing the hybrid gene HSVtk::Sh and the cDNA of pol β.

TABLE 3

| E. coli | Survival (%) 37° C. | 42° C. | Zeocine 25 μg/ml | AZT 10 μg/ml |
|---|---|---|---|---|
| SC 18-12 | 100 | 5 | 5 | ND |
| SC 18-12/pZHTkβ | 90 | 50 | 97 | ND |
| SC 18-12 tk⁻ | ND | ND | ND | 100 |
| SC 18-12 tk⁻/pZHTkβ | ND | ND | ND | 2 |
| TD205 | 100 | 11 | ND | ND |
| TD205/pZHTkβ | 100 | 78 | ND | ND |

EXAMPLE 4

Sensitivity to ddC of mouse melanoma cells transfected with pUTpolβ

Highly metastatic cancer cells of mouse melanomas, B16 cells, were transfected with the vector pUT-pol β by the DMSO/polybrene method.

Recombinant cell extracts were prepared and then analyzed by Western blotting against anti-polβ antibodies. This experiment showed the overexpression of pol β in the transfected cells. We also showed during DNA replication tests that these extracts allowed an in vitro incorporation of triphosphorylated ddC into the G-rich nucleotide substrate:

3'CATACGAGAACCAACAT 5' (SEQ ID NO:5)

5' GGTGGTGGTGGGCGCCGGCGGTGTGAAT-TCGGCACTGGCCGTCGTATGCTCTTGGTTGTA 3' (SEQ ID NO:6)

This result shows the specificity of pol β in the incorporation of ddC into DNA, leading to blocking of the replication of this DNA.

FIG. 4 shows the toxicity of ddC on B16 cells transfected with pUT-pol β relative to cells transfected with a control vector pUT526Δ containing no polβ but only the selection gene Sh. The cell survival was measured by staining the treated cells with Giemsa in order to compatibilize those cells which survived being placed in contact with the drugs.

EXAMPLE 5

Mouse melanoma cells transfected with pUT-pol β are sensitized to AZT.

Experiments similar to the ones above were carried out using AZT.

FIG. 5 shows the toxic effect of AZT on cells transfected with pUT-pol β.

EXAMPLE 6

Mouse melanoma cells which express HSV TK::Sh and Pol β are more sensitive to AZT than cells which express HSV TK::Sh or Pol β separately.

B16 cells were transfected with the vector pZHTkβ which co-expresses Pol β and an HSV TK::Sh protein by fusing, HSV TK expressing the thymidine kinase (TK) and thymidilate kinase (TMK) activities of the herpesvirus HSV-1, i.e. capable of mono- and then diphosphorylating thymidine and also a wide range of nucleoside analogs, the protein Sh which confers resistance to zeocine.

FIG. 6 shows that these cells are more sensitive to AZT than cells which express Pol β::Sh or HSV TK::Sh separately.

REFERENCES CITED

1. Culver, K. W., Van Gilder, J., Link, C. J., Carlstrom, T., Buroker, T., Yuh, W., Koch, K., Schabold, K., Doornbas, S. and Wetjen, B. Gene therapy for the treatment of malignant brain tumors with in vivo tumor transduction with the herpes simplex thymidine kinase gene/ganciclovir system. Hum. Gene Ther., 5:343–379, 1994.

2. Moolten, F. L. and Wells, J. M. Curability of tumors bearing herpes thymidine kinase genes transferred by retroviral vectors. J. Natl. Cancer Inst., 82:297–300, 1990.

3. Culver, K. W., Ram, Z. Wallbridge, S., Ishii, H., Oldfield, E. H. and Blaese, R. M. In vivo gene transfer with retroviral vector-producer cells for treatment of experimental brain tumors. Science, 256:1550–1552, 1992.

4. Huber, B. E., Richards, C. A. and Krenitsky, T. A. Retroviral-mediated gene therapy for the treatment of hepatocellular carcinoma: an innovative approach for cancer therapy. Proc. Nat. Acad. Sci. USA, 88:8039–8043, 1991.

5. Mroz, P. J. and Moolten, F. L. Retrovirally transduced *Escherichia coli* gpt genes combine selectability with chemosensitivity capable of mediating tumor eradication. Hum. Hene Ther, 4:589–95, 1993.

6. Mullen, C. A., Kilstrup, M. and Blaese, R. M. Transfer of the bacterial gene for cytosine deaminase to mammalian cells confers lethal sensitivity to 5-fluorocytosine: a negative selection system. Proc. Natl. Acad. Sci. USA, 89:33–7, 1992.

7. Vile, R. G. and Hart, I. A. Use of tissue-specific expression of the herpes simplex virus thymidine kinase gene to inhibit growth of established murine melanomas following direct intratumoral injection of DNA. Cancer Res. 53:3860–3864, 1993.

8. Kornberg, A. and Baker, T. Eukaryotic DNA polymerases. In: DNA replication, 2nd ed., pp. 197–225. New York: Freeman, W. H., 1992.

9. Sobol, R. W., Horton, J. K., Kuhn, R., Gu, H., Singhal, R. K., Prasad, R., Rajewsky, K. and Wilson, S. H. Requirement of mammalian DNA polymeraseβ in base-excision repair. Nature, 379:183–186, 1996.

10. Jenkins, T. M., Saxena, J. K., Kumar, A., Wilson, S. H. and Ackerman, E. J. DNA polymerase β and DNA synthesis in Xenopus oocytes and in a nuclear extract. Science, 258:475–478, 1992.

11. Sweasy, J. B. and Loeb, L. Mammalian DNA polymerase β can substitute for DNA polymerase I during DNA replication in *Escherichia coli*. J. Biol. Chem., 267:1407–1410, 1992.

12. Zmudzka, B. Z., Fornace, A., Collins, J. and Wilson, S. H. Characterisation of DNA polymerase β mRNA : cell-cycle and growth response in cultured human cells. Nucleic Acids Res., 16 : 9589–9596, 1988.

13. Srivastava, D. K., Rawson, T. Y. Showalter, S. D. and Wilson, S. H. Phorbol ester abrogates up-regulation of DNA polymerase β by DNA-alkylating agents in Chinese Hamster Ovary cells. J. Biol. Chem., 270: 16402–16408, 1995.
14. Fornace, A. J., Zmudzka, B., Hollander, M. C. and Wilson, S. H. Induction of β-polymerase mRNA by DNA damaging agents in Chinese Hamster Ovary cells. Mol. Cell. Biol. 9:851–853, 1989.
15. Kunkel, T. A. Frameshift mutagenesis by eucaryotic DNA polymerases in vitro. J. Biol. Chem., 261:13581–13587, 1986.
16. Copeland, W. C., Chen, M. S. and Wang, T. S. F. Human DNA polymerases α and β are able to incorporate anti-HIV deoxynucleotides into DNA. J. Biol. Chem., 267:21459–21464, 1992.
17. Parker, W. B., White, E. L., Shaddix, S. C., Ross, L. J., Buckheit, R. W., Germany, J. M., Secrist, J. A., Vince, R. and Shannon, W. M. Mechanisms of inhibition of human immunodeficiency virus type I reverse transcriptase and human DNA polymerases α, β and γ by the 5'-triphosphates of carbovir, 3'azido-3'-deoxythymidine, 2',3'-dideoxyguanosine, and 3'-deoxythymidine. J. Biol. Chem., 266:1754–1762, 1991.
18. Sommadossi, J. P., Carlisle, R. and Zhou, Z. Cellular pharmacology of 3'-azido-3'-deoxythymidine with evidence of incorporation into DNA of human bone marrow cells. Mol. Pharmacol., 36:9–14, 1989.

What is claimed is:

1. An expression vector comprising a polynucleotide sequence encoding DNA polymerase β and a polynucleotide sequence encoding thymidine kinase or thymidilate kinase, wherein said polynucleotide sequences are under the control of an expression system which is effective in expressing said polymerase β in a cell.

2. The vector according to claim 1, wherein the vector is a viral vector derived from a virus selected from the group consisting of an adenovirus, adeno-associated virus, retrovirus, herpesvirus, poxvirus, parvovirus, plasmovirus, Semliki Forest virus, and Sinbis virus.

3. The vector of claim 1 which is pZH tk pol β.

4. An isolated cell which is transformed with the expression vector according to claim 1.

5. A pharmaceutical composition comprising the expression vector according to claim 1 and at least one nucleoside analog.

6. The pharmaceutical composition according to claim 5, wherein said nucleoside analog is AZT or ddC.

7. A pharmaceutical composition comprising an expression vector comprising a polynucleotide sequence encoding DNA polymerase β and at least one nucleoside analog, wherein said polynucleotide sequence is under the control of an expression system which is effective in expressing said DNA polymerase β and induces overproduction of said DNA polymerase β in tumor cells or cells infected by a virus.

8. The pharmaceutical composition according to claim 7, further comprising an expression vector comprising a polynucleotide sequence coding for thymidine kinase or thymidilate kinase which is under the control of an expression system which is effective for the expression of said thymidine kinase or thymidiiate kinase in sad cell.

9. The pharmaceutical composition according to claim 8, wherein said nucleoside analog is AZY or ddC.

10. The pharmaceutical composition according to claim 7, wherein said nucleoside analog is AZT or ddC.

11. A method for enhancing the capability of a tumor cell in incorporating a nucleoside analog having antiviral or antitumor activity into DNA of said cell, comprising introducing directly into said cell with an expression vector, thereby inducing overproduction of DNA polymerase β in said cell, wherein said expression vector comprises a polynucleotide sequence encoding DNA polymerase β under the control of an expression system which is effective in expressing said DNA polymerase β and induces overproduction of said DNA polymerase β in said tumor cell.

12. The method according to claim 11, wherein said vector is used in combination with a vector expressing thymidine kinase or thymidilate kinase.

13. The method according to claim 11, wherein said vector is used in combination with at least one nucleoside analog.

* * * * *